US00PP23786P2

(12) United States Plant Patent
Klemm et al.

(10) Patent No.: US PP23,786 P2
(45) Date of Patent: Jul. 30, 2013

(54) POINSETTIA PLANT NAMED 'NPCW12202'

(50) Latin Name: ***Euphorbia pulcherrima* Willd. ex Klotzsch**
Varietal Denomination: NPCW12202

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 7 days.

(21) Appl. No.: 13/385,475

(22) Filed: Feb. 22, 2012

(51) Int. Cl.
*A01H 5/00* (2006.01)

(52) U.S. Cl.
USPC ..... Plt./304

(58) Field of Classification Search
USPC ..... Plt./304
See application file for complete search history.

*Primary Examiner* — Kent L Bell
(74) *Attorney, Agent, or Firm* — Jondle Plant Sciences Division of Swanson & Bratschun, L.L.C.

(57) ABSTRACT

A new poinsettia plant particularly distinguished by creamy white colored bracts.

1 Drawing Sheet

Genus and species: *Euphorbia pulcherrima* Willd. ex Klotzsch
Variety denomination: 'NPCW12202'.

BACKGROUND OF THE NEW PLANT

The present invention comprises a new and distinct variety of poinsettia plant, botanically known as *Euphorbia pulcherrima* Willd. ex Klotzsch and hereinafter referred to by the variety name 'NPCW12202'. The new variety is the result of cross conducted in November 2006 in Kenya, district of Nairobi, between the female parent poinsettia plant 'KLEW01066' (U.S. Plant Pat. No. 13,621) and the male poinsettia plant 'P 212' (unpatented). A single plant selection was subsequently chosen for further evaluation and asexual propagation.

'NPCW12202' was first propagated via vegetative cuttings in Stuttgart, Germany in October 2007 and has been asexually reproduced by vegetative cuttings in Stuttgart, Germany for approximately 12 generations. 'NPCW12202' has been found to retain its distinctive characteristics through successive asexual propagations via vegetative cuttings.

'NPCW12202' has not been sold or made publicly available more than one year prior to the filing date of this application.

SUMMARY OF THE INVENTION

The most outstanding and distinguishing characteristic of this new variety when grown under normal horticultural practices in Stuttgart, Germany is a warm creamy white bract color.

DESCRIPTION OF THE PHOTOGRAPH

This new poinsettia plant is illustrated by the accompanying photograph; the colors shown are as true as can be reasonably obtained by conventional photographic procedures.

The photograph is of a whole plant about four-months-old and in full flower.

DESCRIPTION OF THE NEW VARIETY

The following detailed description sets forth the distinctive characteristics of 'NPCW12202'. The data which define these characteristics was collected from asexual reproductions carried out in Stuttgart, Germany. The plant history was taken on four month-old plants grown in 13 centimeter pots from August to December 2011 with a pinch date at week 31. The plants were grown in a greenhouse covered with glass. Color readings were taken under natural light in the greenhouse. Color references are primarily to the R.H.S. Colour Chart of The Royal Horticultural Society of London (R.H.S.) ($5^{th}$ edition 2007).

DETAILED BOTANICAL DESCRIPTION OF THE NEW PLANT

Classification:
- *Family.*—*Euphorbiaceae.*
- *Botanical.*—*E. pulcherrima* Willd. ex Klotzsch.
- *Common.*—Poinsettia.

Parentage:
- *Female parent.*—'KLEW01066' (U.S. Plant Pat. No. 13,621).
- *Male parent.*—'P 212' (unpatented).

Growth:
- *Time to produce a rooted cutting.*—4 weeks.
- *Blooming habit.*—Intermittent.
- *Flowering response time.*—Approximately 52 days.
- *Keeping quality.*—Very good.

Plant:
- *Form.*—Triangular.
- *Growth habit.*—Upright.
- *Height.*—30.0 cm to 35.0 cm.
- *Width.*—25.0 cm to 30.0 cm.
- *Number of branches.*—6 to 7.
- *Average number of inflorescences per plant.*—6 to 7.

Stems:
- Color: Lower part: RHS 146B. Upper part: RHS 143A.
- *Length.*—Approximately 25.0 cm to 30.0 cm.
- *Internode length.*—2.0 cm to 4.0 cm.
- *Diameter.*—0.5 cm to 1.0 cm.

Leaves:
- *Quantity.*—8 to 15 per lateral branch.
- *Arrangement.*—Alternate.

*Shape.*—Ovate.
*Apex.*—Acute.
*Base.*—Rounded.
*Margin.*—Serrated.
*Lobes.*—Quantity: Medium. Lobation characteristics: Medium depth.
*Texture* (*both surfaces*).—Smooth.
*Vein color* (*both surfaces*).—RHS 142C.
*Variegation.*—Absent.
*Size.*—Length: 4.0 cm to 8.0 cm. Width: 2.0 cm to 7.0 cm.
*Color.*—Mature foliage: Upper surface: RHS 137A and RHS 139A. Lower surface: RHS 137C. Immature foliage: Upper surface: RHS 141A. Lower surface: RHS 139C.
*Leaf petiole.*—Length: Approximately 2.0 cm to 4.0 cm. Diameter: Approximately 0.2 cm to 0.3 cm. Color: Upper surface: RHS 144B. Lower surface: RHS 143C. Texture: Smooth.

Inflorescence:
*Type and habit.*—Intermittent.
*Lastingness of inflorescence on the plant.*—4 to 5 weeks.
*Diameter.*—Approximately 20.0 cm.
*Height.*—2.0 cm to 4.0 cm.
*Fragrance.*—Absent.

Bracts:
*Number of bracts per inflorescence.*—6 to 9.
*Shape.*—Ovate.
*Apex.*—Acute.
*Base.*—Rounded.
*Margin.*—Entire.
*Lobes.*—Shallow.
*Size.*—Length: 7.0 cm to 10.0 cm. Width: 4.0 cm to 6.0 cm.
*Texture* (*both surfaces*).—Smooth.
*Venation pattern.*—Reticulate.
*Vein color.*—Upper surface: Close to RHS 142C. Lower surface: RHS 142C.
*Bract color* (*both surfaces*).—Between RHS 158B and RHS 4D.
*Bract petiole.*—Length: 1.0 cm to 3.0 cm. Diameter: 0.2 cm. Color: Upper surface: Slightly more green than RHS 1C. Lower surface: RHS 142C.

Cyme:
*Diameter.*—1.5 cm to 2.5 cm.
*Cyathia quantity.*—6 to 9 per inflorescence.
*Cyathium.*—Shape: Ovate. Diameter: 0.3 cm to 0.5 cm. Length: 0.6 cm to 0.7 cm. Color: RHS 143C.
*Peduncle.*—Color: RHS 143C. Diameter: 0.3 cm. Length: 0.1 cm to 0.2 cm. Texture: Smooth.
*Nectar cups.*—Shape: Crescentric. Number: 1 per cyathium. Diameter: 0.1 cm when closed, 0.2 cm when open. Length: 0.3 cm to 0.5 cm. Color: RHS 143D when closed, RHS 3B when open.

Reproductive organs:
*Stamens.*—Quantity: 5 to 8 per cyathium. Anther: Shape: Ovate. Length: Less than 0.05 cm. Filaments: Length: 0.25 cm. Color: RHS 155C. Pollen: Quantity: Moderate. Color: RHS 3B.
*Gynoecium.*—Present.
*Pistil quantity per cyathium.*—1.
*Pistil length.*—0.2 cm. Stigma: Shape: Divided into 2 parts. Color: White. Style: Length: 0.2 cm. Color: White.

Fruit and seed set: No fruit or seed have been observed.
Disease and insect/pest resistance: None tested.

COMPARISON WITH PARENTAL AND COMMERCIAL VARIETYS

'NPCW12202' differs from the female parental poinsettia plant 'KLEW01066' (U.S. Plant Pat. No. 13,621) by having creamy white colored bracts and cyathia of average size and quantity, whereas 'KLEW01066' has red colored bracts and larger, more numerous cyathia.

'NPCW12202' differs from the male parental poinsettia plant 'P 212' (unpatented) by having creamy white colored bracts and cyathia of average quantity, whereas 'P 212 has red colored bracts and less cyathia.

'NPCW12202' differs from the commercial variety 'NPCW09124' (Community Plant Variety Rights No. 28156) by having creamy white colored bracts with margins that are entire, whereas 'NPCW09124' has lighter colored bracts with margins that are serrated.

We claim:

1. A new and distinct cultivar of poinsettia plant named 'NPCW12202' as described and shown herein.

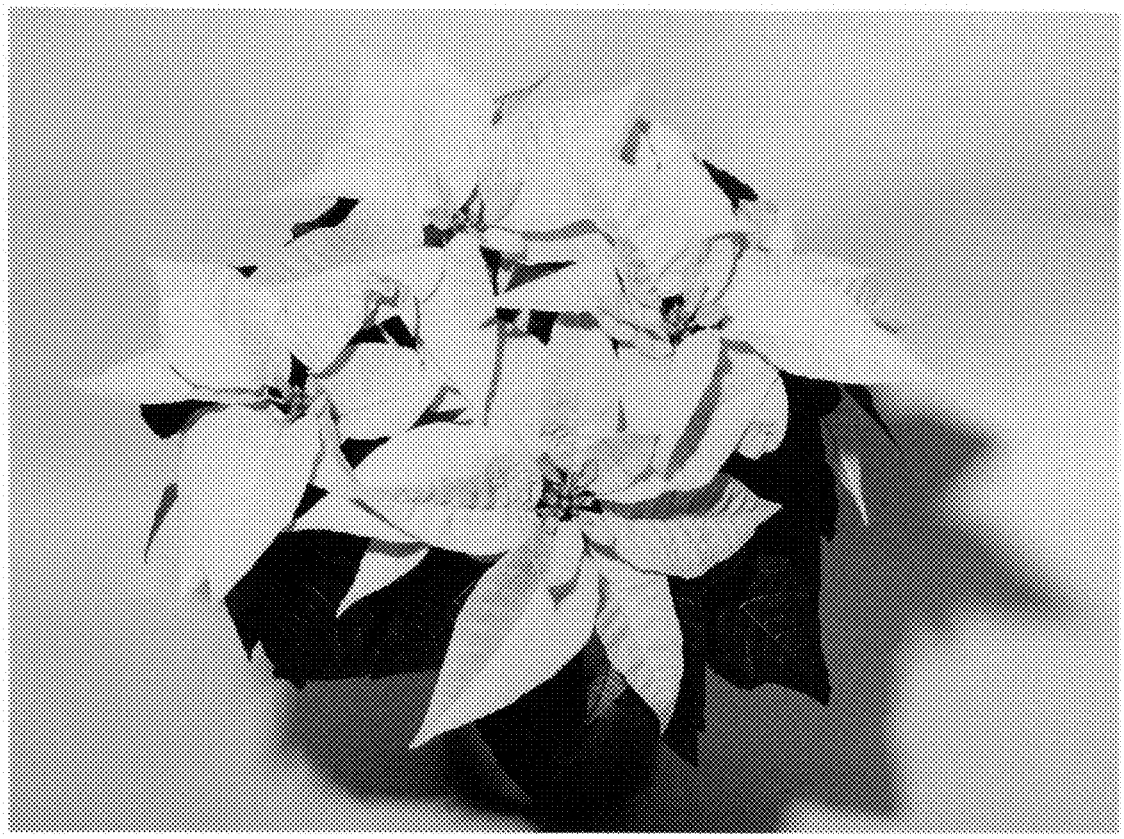

* * * * *